United States Patent [19]

Smith et al.

[11] Patent Number: 5,139,019

[45] Date of Patent: Aug. 18, 1992

[54] LASER REFLECTIVE ENDOTRACHEAL DEVICE

[75] Inventors: James J. Smith; James B. Hissong, both of Jacksonville, Fla.

[73] Assignee: Xomed-Treace Inc., Jacksonville, Fla.

[21] Appl. No.: 661,578

[22] Filed: Feb. 26, 1991

[51] Int. Cl.$^5$ .................... A61M 16/00; A61M 29/00; A62B 9/06

[52] U.S. Cl. .................... 128/207.15; 128/207.14; 128/911; 604/96

[58] Field of Search ............. 128/207.14, 207.15, 128/911; 604/96

[56] References Cited

U.S. PATENT DOCUMENTS

| | | | |
|---|---|---|---|
| 4,378,796 | 4/1983 | Milhaud | 128/207.15 |
| 4,489,722 | 12/1984 | Ferraro et al. | 128/207.15 |
| 4,611,588 | 9/1986 | Laptewicz, Jr. et al. | 128/207.14 |
| 4,632,108 | 12/1986 | Geil | 128/207.14 |
| 4,658,812 | 4/1986 | Hatzenbuhler et al. | 128/207.14 |
| 4,953,548 | 9/1990 | Stoodard et al. | 128/207.14 |

FOREIGN PATENT DOCUMENTS 2557459  6/1977  Fed. Rep. of Germany .............. 128/207.14

OTHER PUBLICATIONS

Feinstein and Zacher, "A New Endotracheal Tube for ENT Laser Surgery", Dept. of Anesthesiology, Washington Un., St. Louis, MO, 63110.

Norton and VOS, "New Endotracheal Tube . . . Larynx", *Ann. Otol.*, 87:1978, pp. 554–557.

Merocel Laser-Guard, Americal Corp., Mystic, CT, 06355, 1-800-MEROCEL, Jul. 12, 1988.

Hawley's Condensed Chemical Dictionary, 11th ed., Sax and Lewis, Sr., Van Nostrand Reinhold Co., NY. ISBN 0-442-28097-1, © 1987, p. 944.

*Primary Examiner*—Edgar S. Burr
*Assistant Examiner*—Kimberly L. Asher
*Attorney, Agent, or Firm*—Stuart E. Krieger

[57] ABSTRACT

An endotracheal device for passing fluids into or out of the body includes a tube member with a laser reflective material in the form of a flexible sheath that is covered by a flexible non-metallic protective covering. The laser reflective material is preferably metallic and can be formed of aluminum, copper, silver or stainless steel. Flexibility of the laser reflective material is obtained by applying the sheath to the tube member in the form of a spiral or in a corrugated form. A protective covering is provided over the laser reflective material and is preferably formed of a polytetrafluoroethylene material. The protective covering, coating or tubular wrapping is applied in a manner which enables such covering to rupture or break when a laser beam strikes the tube. The area of breakage of the protective covering exposes the underlying laser reflective material thereby enabling the laser beam to be reflected away from the tubular member. Such reflection or dissipation of the laser beam avoids heat buildup or heat absorption in the tube member enabling the endotracheal device to avoid burn-through despite a laser strike and minimize any discomfort to a patient.

22 Claims, 3 Drawing Sheets

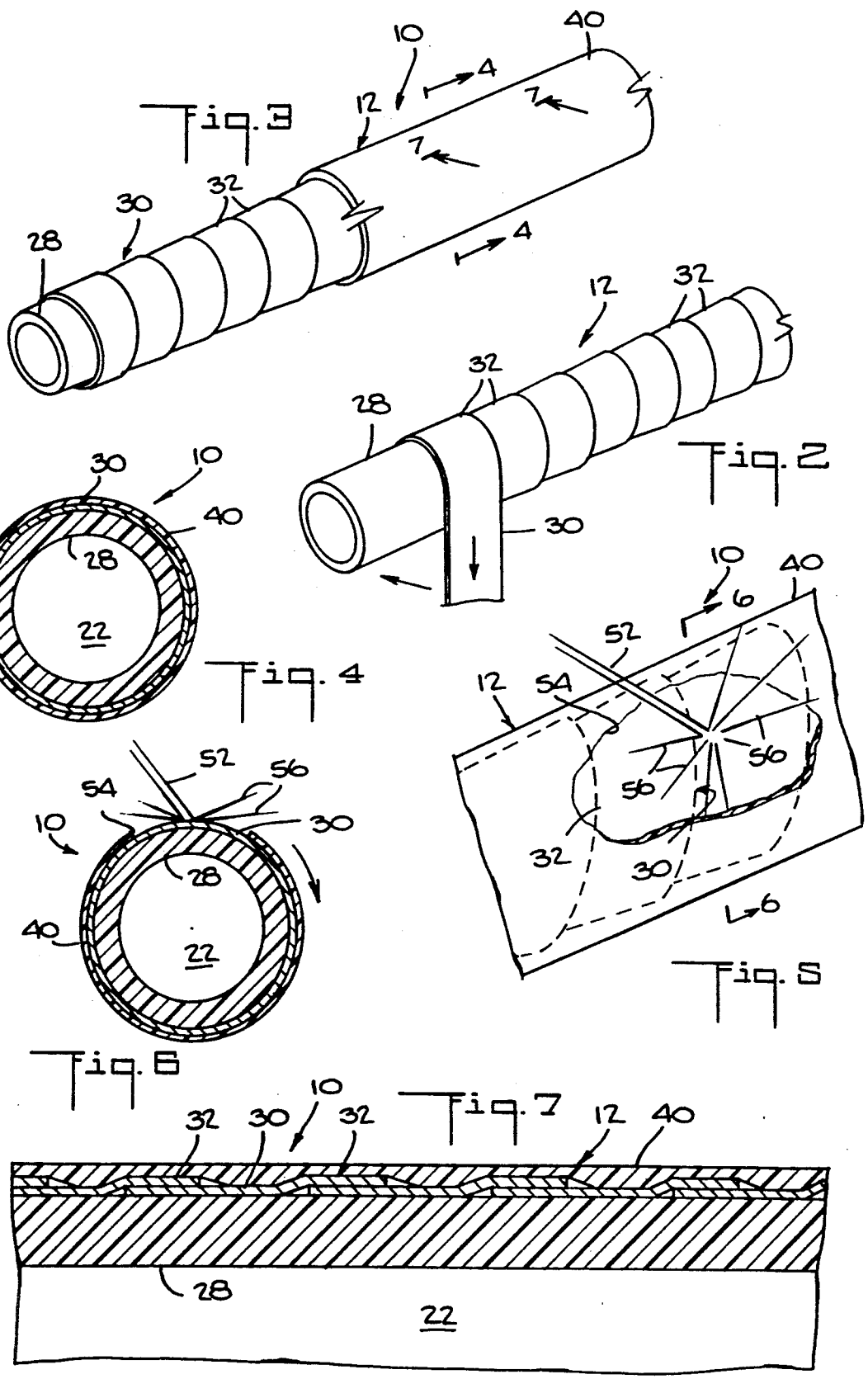

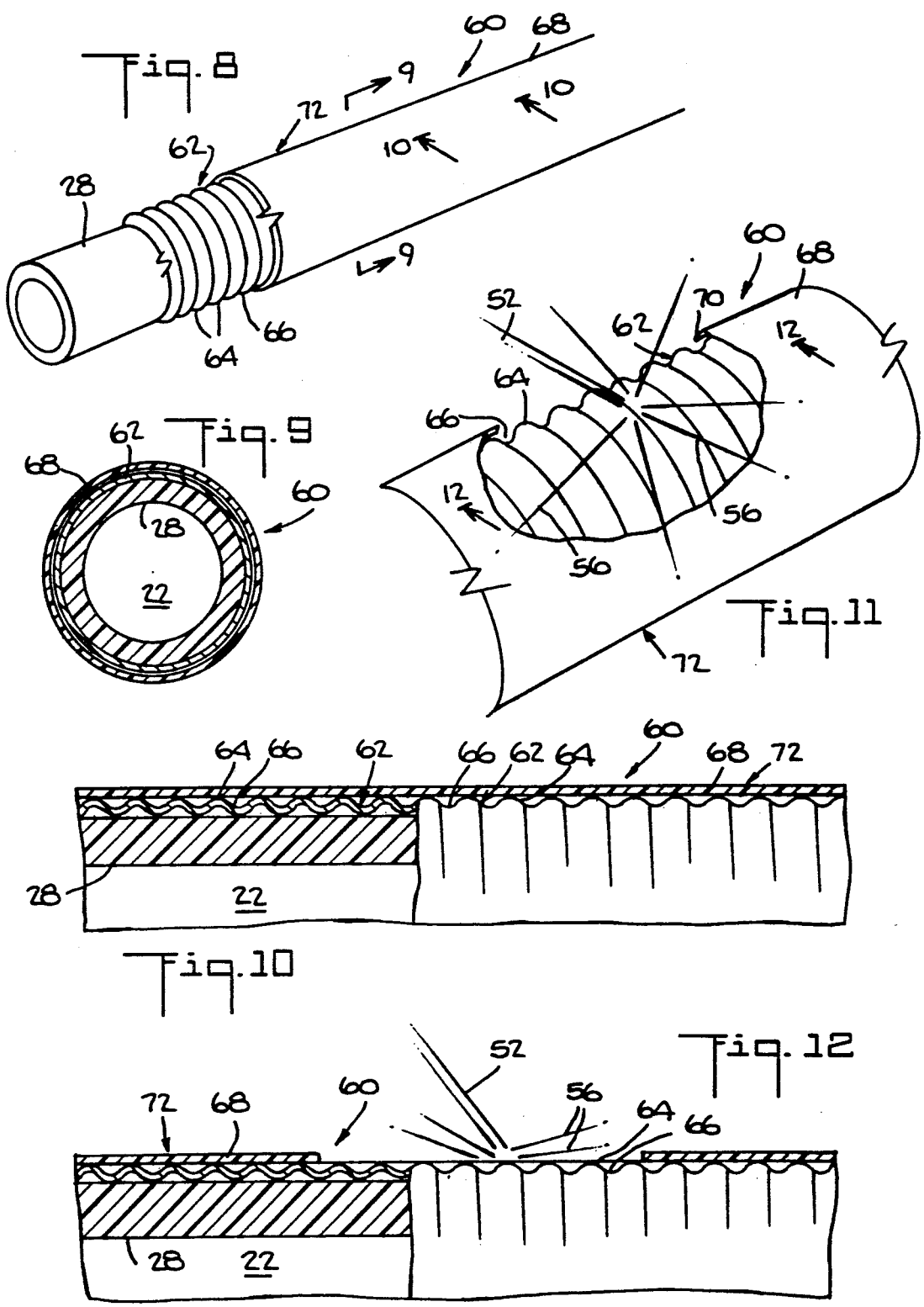

LASER REFLECTIVE ENDOTRACHEAL DEVICE

BACKGROUND OF THE INVENTION

This invention relates to endotracheal devices and more particularly to a laser resistant endotracheal tube with a concealed laser reflection material that can be immediately exposed in response to a laser strike to the tube.

Endotracheal devices are well known for facilitating passage of gases into and out of the body. An endotracheal device is usually placed in a patient's trachea to administer anesthesia and to maintain a respiratory flow path while a patient is under anesthesia.

In many surgical procedures, especially when there is a need to perform a remote cutting operation, a laser is used to cut or remove some portion of tissue. Occasionally a laser beam is inadvertently directed toward an endotracheal tube, thereby concentrating a substantial amount of energy onto the tube. If such energy is not dissipated or redirected, the tube can be burnt through or otherwise damaged, causing discomfort or injury to the patient.

Some known endotracheal devices that dissipate or redirect laser energy to resist laser burn-through include absorption devices, absorption and reflection devices, and reflection devices.

Absorption devices require the laser light to be absorbed by the tube. To accomplish such absorption, a coating of metallic particles mixed with a polymer is bonded to the exterior of a flexible polymeric tube. When the laser strikes the coating, a small amount of light is deflected with the remainder being absorbed into the surrounding incident area. This type of laser-resistant tube is effective with low energy laser strikes and short time exposure to the laser beam.

Absorbing and reflecting endotracheal devices rely on a layer of highly reflective material, typically aluminum or copper, which is, in turn, covered by a coating of laser absorption material of the type previously described. These devices thus rely on the reflective metallic layer to reflect the portion of the laser beam that is not absorbed by the laser absorption coating but penetrates the coating.

Since an endotracheal tube must be flexible for intubation purposes, the reflective metallic layer must also be flexible. Thus, the metallic layer can be in the form of a spirally wound metallic tape or a mechanically corrugated or worked metal. Reflective metals in these forms usually have rough, nonconformal surface characteristics that are an agitant to the patient's trachea and other body parts contacted by the tube.

In some instances, the laser absorptive coating is applied over the laser reflective material and smooths the surface of the reflective material to reduce potential patient trauma due to tracheal contact with a rough, nonconformal surface.

The absorption and reflection type endotracheal device is usually adequate for low laser energy levels over short periods of time. Under more rigorous conditions the absorptive coating tends to char which reduces reflectivity of the laser energy and promotes absorption of more of the laser energy until the tube reaches a temperature that results in a burn-through.

Reflection devices for endotracheal tubes generally include a highly reflective material to laser wavelength light such as aluminum, silver, stainless steel or copper. The reflective material can cover or actually constitute the body of the endotracheal tube. A tube of this type is thus capable of withstanding relatively high energy for several minutes since a laser beam is reflected from the tube with only small amounts of laser energy being absorbed into the metal. However, since such tube also must be formed of a metallic tape or mechanically corrugated or worked metal, the reflective surface is a rough, nonconformal surface that is also an agitant to the patient's trachea and other body parts contacted by the tube.

It is thus desirable to provide an endotracheal device with a laser reflective capability having a tube cover that provides a smooth conformal surface to the endotracheal tube and does not inhibit the reflectivity of the laser resistant materials.

OBJECTS AND SUMMARY OF THE INVENTION

Among the several objects of the invention may be noted the provision of a novel endotracheal device for passing fluids into or out of the body, a novel endotracheal device that incorporates a sheath of laser reflective material, a novel endotracheal device that includes a laser reflective sheath covered by a smooth conforming cover material that breaks or ruptures when struck by a laser beam, a novel endotracheal device that incorporates a laser reflective material and a protective covering that resists charring if struck by a laser beam, and a novel method of ensuring the integrity of an endotracheal tube that is subject to a potential laser strike.

Other objects and features of the invention will be in part apparent and in part pointed out hereinafter.

In accordance with the invention, the endotracheal device includes a tube member provided with a cuff for stabilizing the device in a trachea, in a predetermined position.

The tube member includes a flexible conduit portion wrapped with a sheath of laser reflective material such as aluminum, copper, silver or stainless steel. The sheath is arranged on the conduit portion in a spiral or corrugated form, for example, so as to assure flexibility of the tube member. The laser reflective material extends substantially the entire length of the tube member, but does not overlay the cuff portion.

A smooth flexible protective covering surrounds the laser reflective material so as to provide a smooth conformal exterior surface for the tube member. The protective covering is preferably a non-metallic material that is capable of rupturing or breaking and shrinking when struck by a laser beam to expose the underlying reflective material. A material such as polytetrafluoroethylene, also known as TEFLON, has been found suitable for this purpose.

Thus, the heat of the laser beam ruptures or breaks the protective covering rather than causing the covering to char. Under this arrangement, the protective covering, at the area of a laser beam strike, exposes the laser reflective material to enable the laser beam to be reflected away from the tube member, thereby preventing the buildup of heat in the tube member when such tube member is subject to a laser strike.

The protective covering, which can be a coating, a tubular wrap or a shrink wrap covering, may be mechanically stressed by stretching during application or have an inherent molecular structure such that when heat and thermal stresses are applied to the coating or covering or wrapping such stresses cause the protective layer to rupture and break without charring when struck by a laser. Such rupture or break occurs almost instantly after a laser strike so that charring and any heat absorption that might be attributable to charring is substantially nonexistent.

The invention accordingly comprises the constructions and method hereinafter described, the scope of the invention being indicated in the claims.

DESCRIPTION OF THE DRAWINGS

In the accompanying drawings,

FIG. 2 is an enlarged fragmentary perspective detail of a laser reflective sheath being spirally wound on a tube member thereof;

FIG. 3 is a view similar to FIG. 2 showing a protective covering provided over the laser reflective sheath thereof;

FIG. 4 is a sectional view taken on the line 4—4 of FIG. 3;

FIG. 5 is a fragmentary detail view thereof showing the incident and reflected area of a laser strike to the endotracheal device which results in a rupturing of the protective covering to expose the underlying layer of the laser reflective sheath material;

FIG. 6 is a sectional view thereof taken on the line 6—6 of FIG. 5;

FIG. 7 is a sectional view thereof taken on the line 7—7 of FIG. 3;

FIG. 8 is a fragmentary detail view of another embodiment of the invention wherein a laser protective sheath is in the form of a corrugated material, the laser protective sheath and the protective layer being partially broken away to show the relationship of each layer to the underlying conduit portion thereof;

FIG. 9 is a sectional view taken on the line 9—9 of FIG. 8;

FIG. 10 is a sectional view taken on the line 10—10 of FIG. 8;

FIG. 11 is a fragmentary detail view thereof showing the incident and reflected area of a laser strike to the endotracheal device which results in a rupturing of the protective covering to expose the underlying layer of laser reflective sheath material;

FIG. 12 is a sectional view taken on the line 12—12 of FIG. 11; and,

Corresponding reference characters indicate corresponding parts throughout the several views of the drawings.

DETAILED DESCRIPTION OF THE INVENTION

Figure 1:
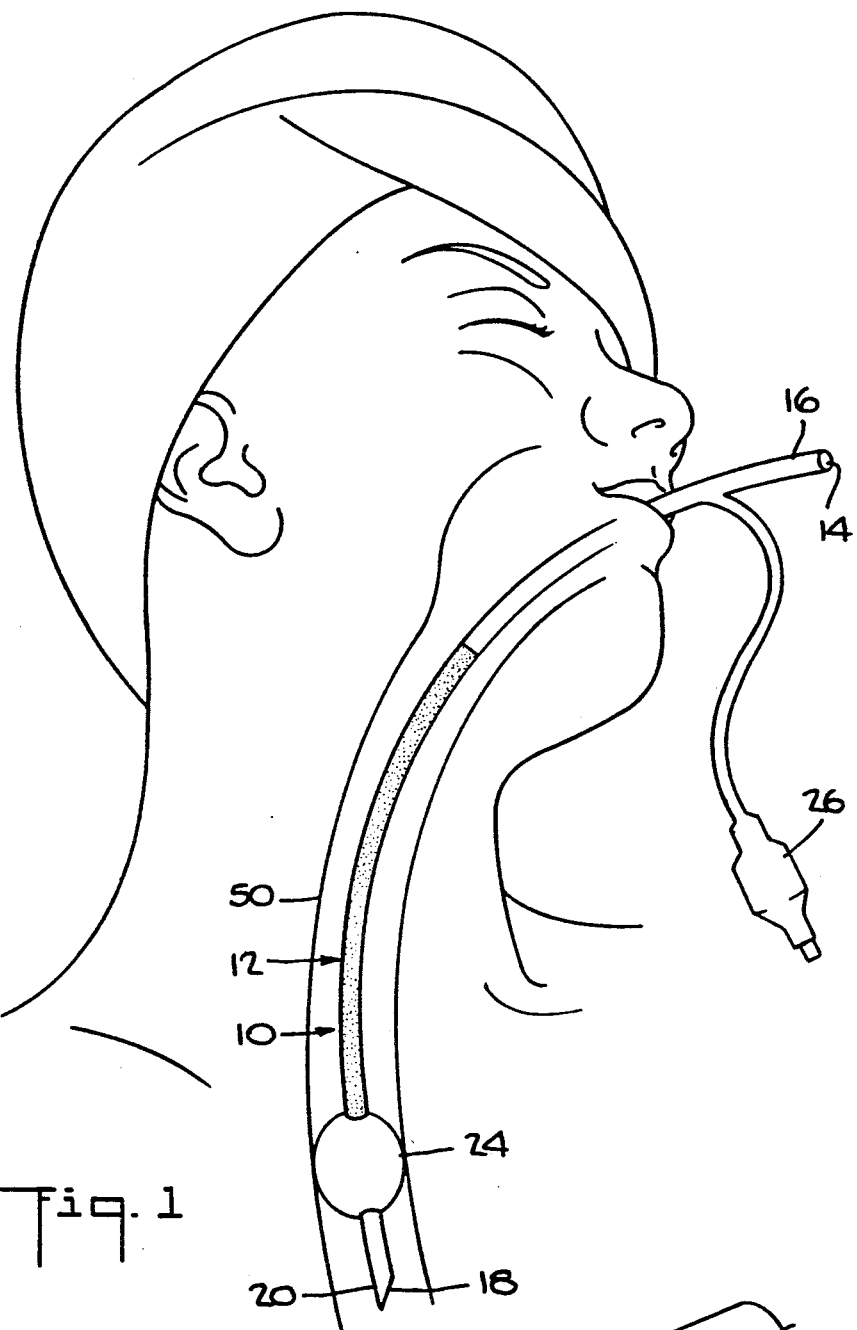
FIG. 1 is a simplified schematic view of an endotracheal device incorporating one embodiment of the invention, positioned in a tracheal passage.

An endotracheal device incorporating one embodiment of the invention is generally indicated by the reference number 10 in FIG. 1.

Referring to FIG. 1, the endotracheal device 10 includes a tube member 12 having an inlet opening 14 at a proximal end portion 16 and an outlet opening 18 at a distal end portion 20. The inlet and outlet openings 14 and 18 communicate through a main fluid passage 22 (FIG. 7) formed within the tube member 12.

A flexible cuff 24 is provided on the tube member 12 near the distal end portion 20. The cuff 24 can be inflatable through an inflation lumen (not shown) in the tube member 12 which communicates with a pilot balloon 26 as shown in FIG. 1.

Referring to FIG. 3, the tube member 12 includes a flexible conduit portion 28 that can be formed of any suitable biocompatible material such as flexible silicone. A ribbon of laser reflective material 30 is spirally wound on the conduit portion 28 from the proximal end 16 to the distal end 20 to constitute the tube member 12 with a flexible metallic sheath. Thus, the spiral wound laser reflective material 30 defines individual spiral segments 32 that are stepped upon each other so as to provide an uninterrupted shield of the laser reflective material 30.

Preferably, the laser reflective material 30 is formed of aluminum, copper, silver or stainless steel.

The width and thickness of the laser reflective material 30 which ensure flexibility of the tube member 12 is, for example, 0.03-0.06 mm. thick and 5.0-8.0 mm. wide for an aluminum, copper, silver or stainless steel ribbon. The step or overlap of each spiral segment 32 can be approximately 2.5-4.0 mm. If desired, the loose end or last wound spiral segment 32 can be secured to the conduit 22 by a band of TEFLON material (not shown) that is shrink wrapped around such segment.

The conduit portion 22 can have an internal diameter of approximately 4.0-8.0 mm., and an external diameter of approximately 5.0-10.0 mm.

Referring to FIG. 7, a protective covering 40 of flexible non-metallic material that is capable of rupturing or breaking and shrinking when struck by a laser beam is provided in continuous form from the proximal end 16 to the distal end 20 of the tube member 12. Preferably the protective covering is formed of an expanded polytetrafluoroethylene (PTFE). The expanded polytetrafluoroethylene, such as sold under the trademark TEFLON, when viewed under a microscope, has an expanded, foamed or layered cobweb-like structure that is broken when a laser beam strikes the covering 40. Preferably the expanded PTFE has a specific gravity of approximately 0.7 and a thickness of approximately 0.08 to 1.2 mm. Accordingly, the continuity of the covering 40 is broken when struck by a laser and facilitates exposure of the underlying laser reflective material 30 to permit almost instantaneous reflection of a laser beam from the tube member 12.

Figure 13:
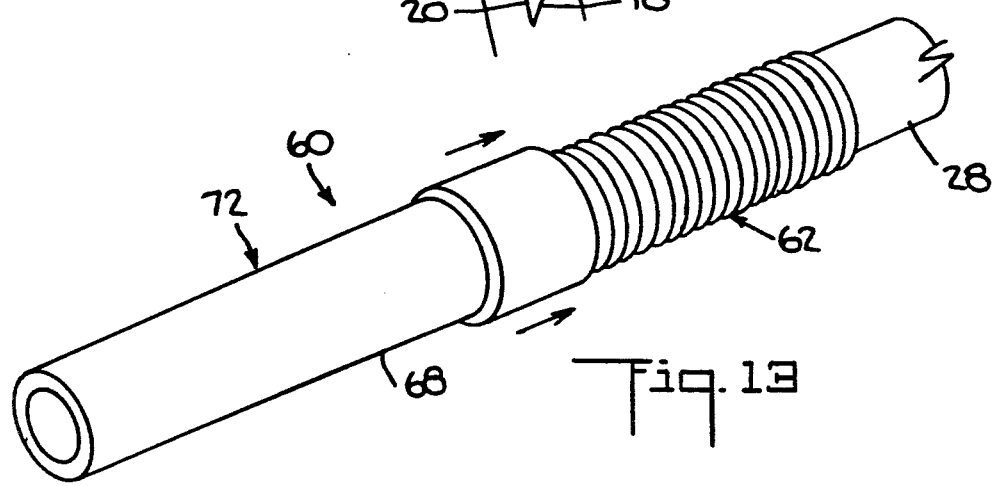
FIG. 13 is a simplified perspective view thereof showing the protective layer being wrapped over the laser reflective sheath.

To enhance the ability of the polymer's microscopically porous structure to pull away from the laser strike point without leaving a char, the covering 40 may be stretched over or unrolled onto the conduit 22 in the manner shown in FIG. 13. The covering 40 also helps assure the stability of the spiral sheath 30 on the conduit 22. The covering 40, while on the conduit 22, is stressed such that when contacted by an incident laser beam, will thus separate at the contact area and relax to an unstressed state.

The protective covering 40 provides a smooth conformal continuous surface over the laser reflective material 30 to render the tube member 12 with a smooth, non-abrasive surface that provides improved patient comfort without sacrificing the protection afforded by the laser reflective material 30.

Preferably, the laser reflective material 30 and the protective covering 40 are applied after the flexible cuff 24 is installed. However, in some instances it may be desirable to install the cuff 24 after the laser reflective material 30 and the protective cover 40 are installed.

In using the endotracheal device 10, the tube member 12 is disposed in a tracheal passage 50, as shown in FIG.

1, in any suitable known manner such that the proximal end 16 is open to ambient air and, if desired, is accessible for connection to an oxygen and anesthetic supply (not shown).

The distal end portion 20 of the endotracheal device 10 is passed through the trachea 50 to locate the cuff 24 at a predetermined position.

During surgery, a laser device (not shown) is often used to perform some or all of the tissue cutting. In some instances the path of the laser beam may interfere with the endotracheal device 10 causing the laser beam to strike a portion of the endotracheal tube member 12. Should a laser beam such as indicated schematically by the reference number 52 (FIG. 5) strike the tube member 12, the heat from the laser beam 52 will cause the protective covering 40 to rupture, break, or open as indicated at 54 with substantially no charring. The polymer's microscopic porosity and low density coupled with stretching or stressing at the time of assembly will provide exposure. Thus, the break or opening 54 in the protective covering 40 exposes the underlying laser reflective material 30 to enable the laser beam 52 to be reflected away from the tube member 12 as shown by the reflected beams 56. The low density of the protective covering 40 assures that there will be little material at any given point with which to leave a char. PTFE works well due to its nonflammability characteristics.

Once the energy of the laser beam is redirected elsewhere from the tube member 12, the tube member will cease absorbing laser energy and will not heat up to a troublesome level. Operability of the endotracheal device is thus assured and patient discomfort is minimized.

A further embodiment of the endotracheal device is generally indicated by the reference number 60 in FIG. 8. The endotracheal device 60 is essentially similar to the endotracheal device 10 as indicated by corresponding reference characters. However, the endotracheal device 60 includes a corrugated laser reflective material 62 rather than the spirally wound laser reflective material 30. The laser reflective material 62, which is the same type of material as the laser reflective material 30, is a continuous corrugated tubular structure that is initially applied in sheet form onto the underlying conduit portion 28. The laser reflective material 62 is thus in the form of a corrugated tubular sheath on underlying conduit portion 28 and can be stabilized thereon in a manner similar to that previously described for the endotracheal device 10.

As most clearly shown in FIGS. 10 and 12, the laser reflective material 62 includes alternate corrugation ribs 64 and corrugation valley portions 66. The corrugation ribs 64 can have a rib thickness of 0.05-2.0 mm. in the radial direction and a rib width of 0.05-2.0 mm. in the axial direction of the tube 72. The corrugation valley portions can have a valley thickness of 0.05-2.0 mm. in the radial direction and a valley width of 0.05-2.0 mm. in the axial direction of the tube 72.

The endotracheal device 60 also includes an overlying protective covering 68 similar to the protective covering 40 which can be applied as a coating or a tubular wrap in the manner previously described for the endotracheal device 10.

As shown in FIG. 13, the protective covering 68 can be unrolled over the laser reflective material 62.

The endotracheal device 60 is used in a manner similar to that previously described for the endotracheal device 10. Thus, when a laser beam 52 as shown in FIG. 11 impinges upon the device 60, the protective covering 68 ruptures or breaks as shown at 70, to expose the underlying layer 62 of the laser reflective material. The laser beam 52 can thus be reflected as shown at 56 away from the laser reflective material 62. Thus, the tube member 72 of the endotracheal device 60, which tube member is constituted by the conduit portion 28, the laser reflective material 62 and the protective covering 68, can resist laser burn-through.

It should be noted that the corrugations enable the tube member 72 to remain flexible, and the protective covering 68 provides a smooth conforming surface over the tube member 72 to provide a minimum agitant surface for patient contact, thus enhancing the comfort of the laser reflective endotracheal device.

Some advantages of the present invention evident from the foregoing description include an endotracheal device which provides almost instantaneous reflection of a laser beam without causing adverse heat buildup in a tube member of the device. Thus the endotracheal device does not absorb excess amounts of energy which can cause burn-through, or through heat buildup cause discomfort to a patient. The substantially instantaneous rupturing or breakage of a protective covering surrounding the laser reflective material prevents charring of such material and helps assure that the integrity of the endotracheal device is maintained even after a laser strike.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An endotracheal device comprising a flexible tube member having opposite end portions and a fluid flow lumen for conducting the flow of fluid from one of the end portions to the other end portion, a cuff member joined to a predetermined peripheral surface portion of said tube member to lodge said cuff and said tube member in a substantially fixed position in a body passage, said tube member including a flexible sheath of laser reflective material for reflecting a laser beam, and a substantially continuous flexible, non-water absorbent, non-metallic, smooth covering for covering said flexible metallic sheath with a smooth conformal surface such that said flexible metallic sheath is disposed immediately beneath said external covering, and said covering extends continuously over said flexible metallic sheath, said covering being formed of a shrinkable rupturable material that shrinks and ruptures in response to a laser strike at the area of said laser strike when a laser beam impinges on said tube member such that said covering exposes the underlying laser reflective material to permit reflection of said laser beam from said tube member.

2. An endotracheal device as claimed in claim 1 wherein said laser reflective sheath is formed as a corrugated layer.

3. An endotracheal device as claimed in claim 1 wherein said laser reflective sheath is formed as a spirally wound layer.

4. An endotracheal device as claimed in claim 1 wherein said laser reflective material is selected from the group consisting of aluminum, copper, silver and stainless steel.

5. An endotracheal device as claimed in claim 1 wherein said flexible non-metallic covering has shrinkage properties attributable to the relief of stresses induced by mechanical means.

6. An endotracheal device as claimed in claim 1 wherein said flexible, non-water absorbent, non-metallic, smooth covering has shrinkage properties attributable to the relief of stresses induced by the molecular structure thereof.

7. An endotracheal device as claimed in claim 1 wherein said flexible, non-water absorbent, non-metallic, smooth covering is formed of polytetrafluoroethylene.

8. An endotracheal device as claimed in claim 1 wherein said flexible, non-water absorbent, non-metallic, smooth covering is in the form of a coating.

9. An endotracheal device as claimed in claim 1 wherein said flexible, non-water absorbent, non-metallic, smooth covering is in the form of a tubular wrapping.

10. An endotracheal device comprising a flexible tube member having opposite end portions and a fluid flow lumen for conducting the flow of fluid from one of the end portions to the other end portion, a cuff member joined to a predetermined peripheral surface portion of said tube member to lodge said cuff and said tube member in a substantially fixed position in a body passage, said tube member including a metallic laser reflecting material spirally wound on substantially the entire periphery of said tube member to provide a flexible metallic laser reflecting layer for said tube member, and a flexible substantially continuous, non-water absorbent, non-metallic, smooth cover layer for covering said metallic layer with a smooth conformal surface, said covering being formed of a shrinkable rupturable material that shrinks and ruptures in response to a laser strike at the area of said laser strike when a laser beam impinges on said tube member such that said covering exposes the underlying laser reflective material to permit reflection of said laser beam from said tube member.

11. An endotracheal device as claimed in claim 10 wherein said flexible, non-water absorbent, non-metallic, smooth covering is a coating of polytetrafluoroethylene.

12. An endotracheal device as claimed in claim 10 wherein said flexible, non-water absorbent, non-metallic, smooth covering is a tubular wrapping of polytetrafluoroethylene.

13. An endotracheal device as claimed in claim 10 wherein said metallic material is selected from the group consisting of aluminum, copper, silver and stainless steel.

14. An endotracheal device comprising a flexible tube member having opposite end portions and a fluid flow lumen for conducting the flow of fluid from one of the end portions to the other end portion, a cuff member joined to a predetermined peripheral surface portion of said tube member to lodge said cuff and said tube member in a substantially fixed position in a body passage, said tube member including a metallic laser reflecting material in the form of a corrugated sheath on substantially the entire periphery of said tube member to provide a flexible metallic laser reflecting layer for said tube member, and a flexible substantially continuous, non-water absorbent, non-metallic, smooth cover layer for covering said metallic layer with a smooth conformal surface, said covering being formed of a shrinkable rupturable material that shrinks and ruptures in response to a laser strike at the area of said laser strike when a laser beam impinges on said tube member such that said covering exposes the underlying laser reflective material to permit reflection of said laser beam from said tube member.

15. An endotracheal device as claimed in claim 14 wherein said flexible, non-water absorbent, non-metallic, smooth covering is a coating of polytetrafluoroethylene.

16. An endotracheal device as claimed in claim 14 wherein said flexible, non-water absorbent, non-metallic, smooth covering is a tubular wrapping of polytetrafluoroethylene.

17. An endotracheal device as claimed in claim 14 wherein said metallic material is selected from the group consisting of aluminum, copper, silver and stainless steel.

18. A method of ensuring the integrity of an endotracheal device having a tube member with opposite ends and a cuff secured to the periphery of the tube, comprising (a) wrapping substantially the entire tube member with a flexible sheath of laser reflective metallic material, (b) covering the flexible metallic sheath smoothly with a continuous covering of a flexible, non-water absorbent, non-metallic heat shrinkable polymer, rupturable in response to a laser strike at the area of said laser strike, and (c) enabling the covering of polymer material to rupture in response to a laser strike by forming the covering with a predetermined thickness and stretch such that when the flexible, non-water absorbent, non-metallic, smooth covering is located on the tube, a laser strike causes the covering to rupture and expose the underlying metallic sheath to the laser beam to permit reflection of the laser beam from the tube member.

19. The method of claim 18 wherein the flexible metallic sheath is selected from the group consisting of aluminum, copper, silver and stainless steel.

20. The method of claim 18 wherein the flexible, non-water absorbent, non-metallic, smooth covering is formed of polytetrafluoroethylene.

21. The method of claim 18 wherein the metallic sheath is applied to the tube member by spirally winding the sheath onto the tube member.

22. The method of claim 18 wherein the metallic sheath is applied to the tube member in the form of a flexible corrugation.

* * * * *